United States Patent
Bai et al.

(10) Patent No.: US 11,111,058 B1
(45) Date of Patent: Sep. 7, 2021

(54) SELF-DESTRUCT-UPON-OPENING CAP APPLICABLE TO SMALL-DIAMETER CONNECTOR USED FOR GASTROINTESTINAL TRACT

(71) Applicant: Baodong Bai, Tianchang (CN)

(72) Inventors: Baodong Bai, Tianchang (CN); Libing Dong, Tianchang (CN); Yuyan Zhou, Tianchang (CN); Xu Dong, Tianchang (CN)

(73) Assignee: Baodong Bai, Tianchang (CN)

( * ) Notice: Subject to any disclaimer, the term of this patent is extended or adjusted under 35 U.S.C. 154(b) by 0 days.

(21) Appl. No.: 16/895,646

(22) Filed: Jun. 8, 2020

(30) Foreign Application Priority Data

Mar. 6, 2020 (CN) .......................... 202010152116.2

(51) Int. Cl.
  *B65D 41/34* (2006.01)
  *A61M 5/50* (2006.01)
  *B65D 55/02* (2006.01)
  *B65D 41/48* (2006.01)
  (Continued)

(52) U.S. Cl.
  CPC ............ *B65D 41/34* (2013.01); *A61J 1/1412* (2013.01); *A61J 1/1418* (2015.05); *A61J 1/1425* (2015.05); *A61M 5/50* (2013.01); *A61M 5/5086* (2013.01); *B65D 41/3414* (2013.01);
  (Continued)

(58) Field of Classification Search
  CPC ... A61J 5/0026; B65D 41/34; B65D 41/3428; B65D 41/62; B65D 41/32; B65D 41/04; B65D 41/0485; B65D 41/3409; B65D 55/022; B65D 2401/15; B65D 2401/35; B65D 50/041; B65D 51/18; B65D 47/10; B65D 47/12; B65D 47/122; B65D 47/123; B65D 47/125; B65D 47/14; B65D 47/142; B65D 47/145; A61M 2005/3104; A61M 5/347; A61M 5/50; A61M 5/5086; A61M 2039/1033; A61M 39/10; A61M 39/20
  USPC .............. 215/251–252, 256, 235; 222/541.1, 222/541.6, 562, 563, 568, 552; 604/110–111; 220/254.1, 255, 256.1,
  (Continued)

(56) References Cited

U.S. PATENT DOCUMENTS

| 2,054,012 A | * | 9/1936 | Teller | ..................... B65D 41/34 215/252 |
| 2,124,874 A | * | 7/1938 | Conner | .............. B65D 41/3404 215/251 |

(Continued)

*Primary Examiner* — J. Gregory Pickett
*Assistant Examiner* — Brijesh V. Patel
(74) *Attorney, Agent, or Firm* — Fenwick & West LLP

(57) ABSTRACT

A self-destruct-upon-opening cap applicable to a small-diameter connector used for a gastrointestinal tract includes a top lid and a cap body. The top lid is arranged on the cap body and fixedly connected to the cap body, and a connecting structure is arranged at one end of the cap body which is not connected to the top lid. The cap body includes a first casing and a second casing. One side of the second casing which is not provided with the connecting structure extends into the first casing, and a top face of the second casing is provided with serrated protrusions in a circumferential direction. The side of the second casing which is not provided with the connecting structure is fixedly connected to the first casing through ribs or contact points. An inner side face of the top lid is provided with grooves matching with the serrated protrusions.

6 Claims, 5 Drawing Sheets

(51) Int. Cl.
*A61J 1/14* (2006.01)
*A61J 15/00* (2006.01)

(52) U.S. Cl.
CPC ......... *B65D 55/022* (2013.01); *A61J 15/0026* (2013.01); *B65D 41/485* (2013.01)

(58) Field of Classification Search
USPC .................. 220/257.1, 258.4–258.5, 288; D24/129–130, 453
See application file for complete search history.

(56) References Cited

U.S. PATENT DOCUMENTS

| | | | | |
|---|---|---|---|---|
| 4,043,334 | A * | 8/1977 | Brown | A61M 5/3134 |
| | | | | 604/199 |
| 4,216,872 | A * | 8/1980 | Bean | B65D 41/485 |
| | | | | 215/353 |
| 4,726,483 | A * | 2/1988 | Drozd | B65D 41/34 |
| | | | | 215/252 |
| 4,941,580 | A * | 7/1990 | Julian | B65D 41/32 |
| | | | | 215/235 |
| 7,316,669 | B2 * | 1/2008 | Ranalletta | A61M 5/3134 |
| | | | | 604/199 |
| 7,632,244 | B2 * | 12/2009 | Buehler | A61M 5/50 |
| | | | | 206/726 |
| D759,486 | S * | 6/2016 | Ingram | D9/453 |
| D797,929 | S * | 9/2017 | Davis | D24/130 |
| D842,464 | S * | 3/2019 | Davis | D24/130 |
| 2016/0067422 | A1 * | 3/2016 | Davis | A61M 5/3202 |
| | | | | 604/192 |
| 2017/0173321 | A1 * | 6/2017 | Davis | A61M 39/10 |

\* cited by examiner

SELF-DESTRUCT-UPON-OPENING CAP APPLICABLE TO SMALL-DIAMETER CONNECTOR USED FOR GASTROINTESTINAL TRACT

CROSS REFERENCE TO RELATED APPLICATIONS

This application claims the priority to Chinese Patent Application No. 202010152116.2 titled "SELF-DE-STRUCT-UPON-OPENING CAP APPLICABLE TO SMALL-DIAMETER CONNECTOR USED FOR GAS-TROINTESTINAL TRACT," filed with the China National Intellectual Property Administration on Mar. 6, 2020, which is hereby incorporated by reference in its entirety.

TECHNICAL FIELD

The present application relates to the technical field of a small-diameter connector used for a gastrointestinal tract, and in particular to a self-destruct-upon-opening cap applicable to a small-diameter connector used for the gastrointestinal tract.

BACKGROUND

There is a great risk in storing sterile pharmaceutical preparations when they have left the pharmacy. For example, in the process that the small-diameter connectors (such as feeders) used for the gastrointestinal tract, after absorbing the sterile pharmaceutical preparations, are transported to the ward (transportation from the pharmacy to the ward), if the traditional caps are used for sealing, since all caps are the same, the authorized doctors in the ward are not able to determine whether the feeders have been used or tampered without records. Therefore, the traditional caps make the feeders be exposed to the risks of cross use or reuse, and even the risks that the pharmaceuticals may be transferred, replaced or abused.

SUMMARY

In view of the above problems in the conventional technology, a self-destruct-upon-opening cap applicable to a small-diameter connector used for a gastrointestinal tract is provided according to the present application, to solve the above technical problems.

In order to achieve the above object, a technical solution provided according to the present application is described as follows.

A self-destruct-upon-opening cap applicable to a small-diameter connector used for a gastrointestinal tract includes a top lid and a cap body, the top lid is arranged on the cap body and is fixedly connected to the cap body, a connecting structure for connecting with a head portion of a feeder used for the gastrointestinal tract is arranged at one end of the cap body which is not connected to the top lid. The cap body includes a first casing and a second casing, the first casing is fixedly connected to the top lid, and the connecting structure is located in the second casing. One side of the second casing which is not provided with the connecting structure extends into the first casing, and a top face of the second casing is provided with serrated protrusions in a circumferential direction. The side of the second casing which is not provided with the connecting structure is fixedly connected to the first casing through ribs or contact points. An inner side face of the top lid is provided with multiple grooves matching with the serrated protrusions, and the serrated protrusions are located inside the grooves. Each of the grooves is a concave slope structure, the grooves are arranged to be in a forward-slanted tooth shape in one direction of the circumferential direction, and in a backward-slanted tooth shape in another reversed direction of the circumferential direction. In a case that the cap is tightly screwed to the feeder (that is, the small-diameter connector) used for the gastrointestinal tract, the grooves of the top lid and the serrated protrusions on the top face of the second casing are mutually engaged and locked. In a case that the cap is screwed off in a reversed direction, the serrated protrusions on the top face of the second casing slide with respect to the grooves of the top lid. In one embodiment, the connecting structure is a threaded structure, preferably a threaded locking structure.

According to the self-destruct-upon-opening cap applicable to the feeder used for the gastrointestinal tract provided in the present application, the cap is required to be connected to the head portion of the feeder for sealing after the feeder absorbs a sterile pharmaceutical preparation, and then the feeder is transported to a ward. In a process of screwing the cap onto the head portion of the feeder, since the grooves of the top lid of the cap and the serrated protrusions on the top face of the second casing are mutually engaged and locked, an acting force during the screwing process is applied mainly to the second casing and the top lid, rather than the ribs (or the contact points) connecting the first casing and the second casing. Therefore, the first casing and the second casing will neither move with respect to each other nor be separated from each other due to the rotation, and thus the cap sealed on the head portion of the feeder remains intact during and after the screwing process. In the process of transporting the feeder sealed by the cap to the ward, in a case that the cap is intentionally opened, since both the grooves of the top lid of the cap and the serrated protrusions on the top face of the second casing are arranged in a forward-slanted tooth shape in the direction that the cap is unscrewed, the serrated protrusions are separated from the grooves during the process that the cap is unscrewed from the head portion of the feeder. When the serrated protrusions and the grooves are separated, a sliding thrust is generated on slanted surfaces where the serrated protrusions and the grooves are in contact with each other. The sliding thrust and a rotating force act on the ribs (or the contact points) between the first casing and the second casing at the same time, causing the fragile ribs or contact points to be broken, and thus the first casing together with the top lid are separated from the second casing, and only the second casing is left for sealing the head portion of the feeder. In this case, when the feeder is transported to the ward, a clinician authorized for feeding in the ward can easily identify whether the feeder has been tampered or not, and if the first casing of the cap is broken or missing, the clinician will immediately find that the feeder has been tampered and will not use it, thus avoiding the risks of cross use or reuse, as well as the risks that pharmaceuticals may be transferred, replaced or abused, and thereby effectively ensuring the safety and reliability of the clinical use of sterile pharmaceutical preparations and feeders.

Another technical solution provided according to the present application is as follows.

A self-destruct-upon-opening cap applicable to a small-diameter connector used for a gastrointestinal tract includes a top lid and a cap body, the top lid is arranged on the cap body and is fixedly connected to the cap body, a connecting structure for connecting with a feeder used for the gastrointestinal tract is arranged at one end of the cap body which is not connected to the top lid. The cap body includes a first casing and a second casing. The first casing is fixedly connected to the top lid, an inner side face of the top lid is provided with serrated protrusions in a circumferential direction. The connecting structure is located inside the second casing, one side of the second casing which is not provided with the connecting structure extends into the first casing, and a top face of the second casing is provided with grooves matching with the serrated protrusions in the circumferential direction. The side of the second casing which is not provided with the connecting structure is fixedly connected to the first casing through ribs or contact points, and the serrated protrusions are located inside the grooves.

According to the self-destruct-upon-opening cap applicable to the feeder used for the gastrointestinal tract provided in the present application, the cap is required to be connected to the head portion of the feeder for sealing after the feeder absorbs a sterile pharmaceutical preparation, and then the feeder is transported to a ward. In a process of screwing the cap onto the head portion of the feeder, since the serrated protrusions of the top lid of the cap and the grooves on the top face of the second casing are mutually engaged and locked, an acting force during the screwing process is mainly applied to the second casing and the top lid, rather than the ribs (or the contact points) connecting the first casing and the second casing. Therefore, the first casing and the second casing will neither move with respect to each other nor be separated from each other due to the rotation, and thus the cap sealed on the head portion of the feeder remains intact during and after the screwing process. In the process of transporting the feeder sealed by the cap to the ward, in a case that the cap is intentionally opened, since both the serrated protrusions of the top lid of the cap and the grooves on the top face of the second casing are arranged in a forward-slanted tooth shape in the direction that the cap is screwed off, the serrated protrusions are separated from the grooves during the process that the cap is unscrewed from the head portion of the feeder. When the serrated protrusions and the grooves are separated, a sliding thrust is generated on slanted surfaces where the serrated protrusions and the grooves are in contact with each other. The sliding thrust and a rotating force act on the ribs (or the contact points) between the first casing and the second casing at the same time, causing the fragile ribs or contact points to be broken, and thus the first casing together with the top lid are separated from the second casing, and only the second casing is left for sealing the head portion of the feeder. In this case, when the feeder is transported to the ward, the clinician authorized for feeding in the ward can easily identify whether the feeder has been tampered or not, and if the first casing of the cap is broken or missing, the clinician will immediately find that the feeder has been tampered and will not use it, thus avoiding the risks of cross use or reuse, as well as the risks that pharmaceuticals may be transferred, replaced or abused, and thereby effectively ensuring the safety and reliability of the clinical use of the sterile pharmaceutical preparations and feeders.

Figure 1:
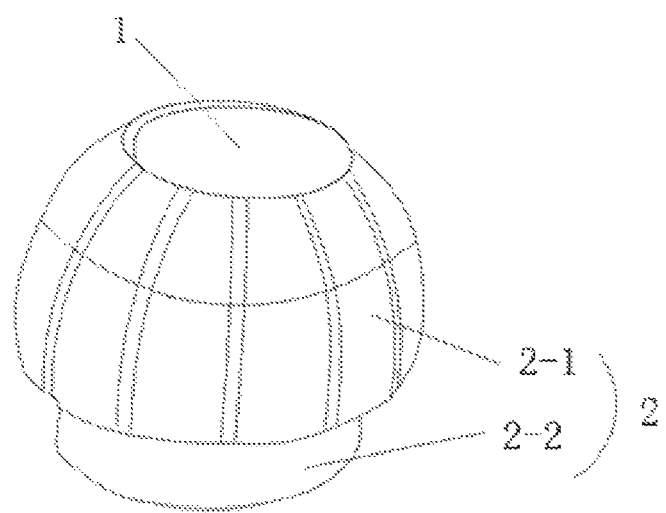
FIG. 1 is a schematic overall structural view of a self-destruct-upon-opening cap applicable to a small-diameter connector used for a gastrointestinal tract according to one embodiment.

| Reference Numerals: | |
|---|---|
| 1 | top lid, |
| 1-1 | groove, |
| 2 | cap body, |
| 2-1 | first casing, |
| 2-2 | second casing, |
| 2-3 | serrated protrusion, |
| 2-4 | contact point, |
| 2-5 | connecting structure. |

DETAILED DESCRIPTION

The present application will be further described in conjunction with the accompany drawings and specific embodiments, so that purposes, technical solutions and advantages of the present application can be more obvious and understandable. It should be understood that the specific embodiments described herein are only intended for interpreting the present application rather than limiting the present application. All other embodiments obtained by those skilled in the art based on the embodiments in the present application without any creative work belong to the scope of protection of the present application.

First Embodiment

Figure 2:
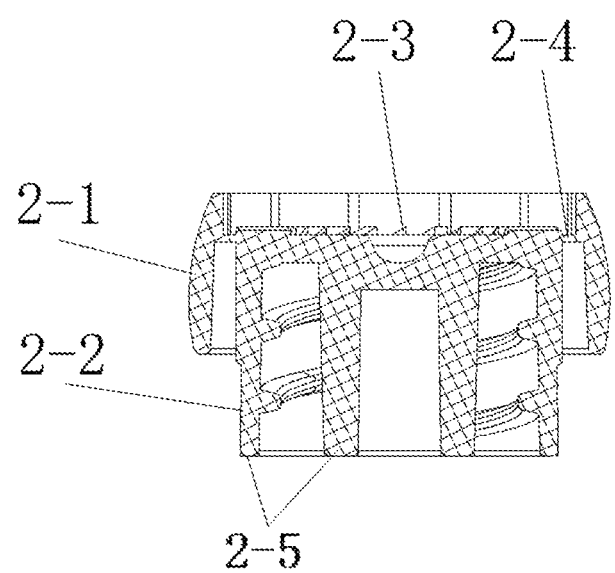
FIG. 2 is a schematic structural view of a cap body according to one embodiment.
Figure 3:
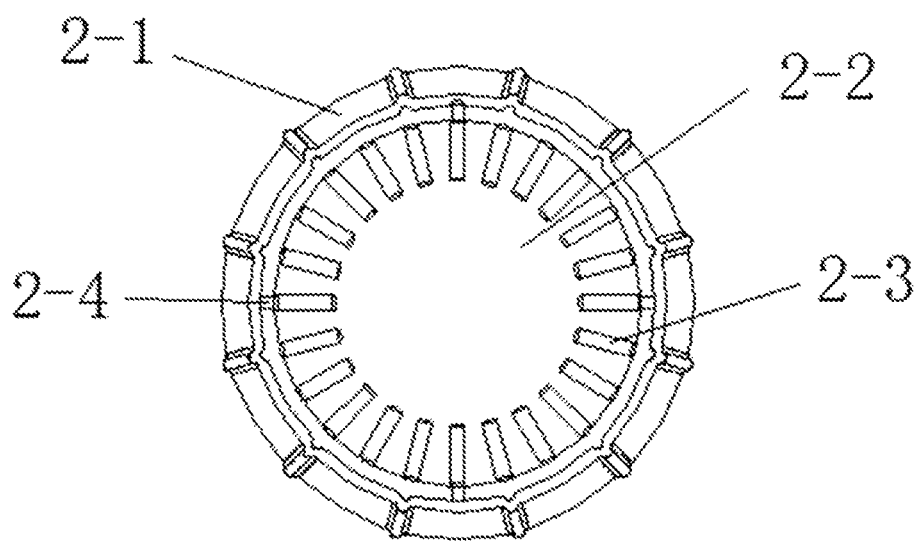
FIG. 3 is a top view of FIG. 2 according to one embodiment.
Figure 4:
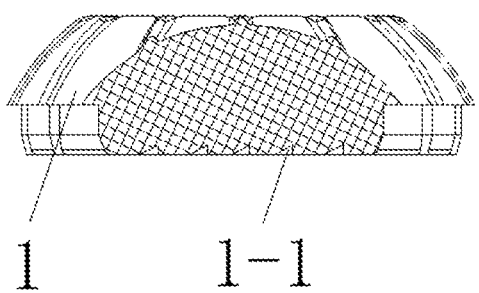
FIG. 4 is a schematic internal structural view of a top lid according to one embodiment.
Figure 5:
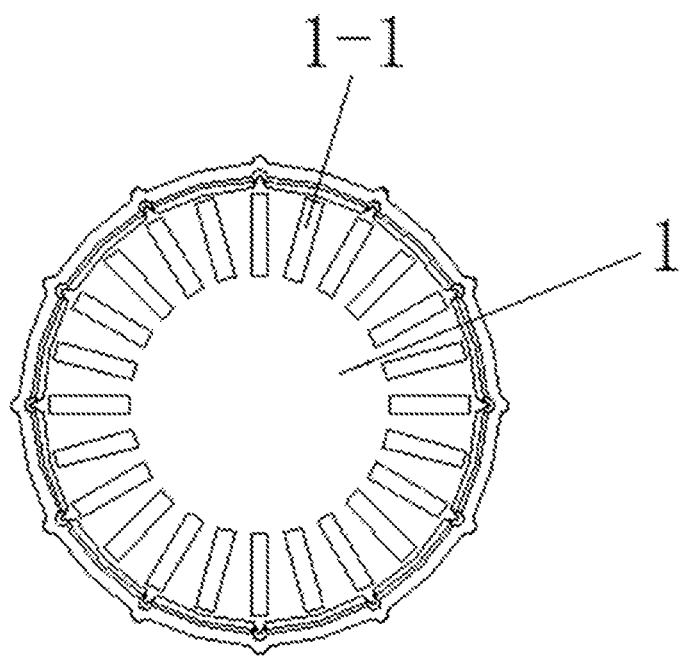
FIG. 5 is a bottom view of FIG. 4 according to one embodiment.

A self-destruct-upon-opening cap applicable to a feeder used for a gastrointestinal tract is provided according to the present application, as shown in FIGS. 1 to 5. The cap includes a top lid 1 and a cap body 2, the top lid 1 is arranged on the cap body 2 and is fixedly connected to the cap body 2, and generally, the top lid 1 and the cap body 2 may be made into an integral structure through ultrasonic thermal bonding. A connecting structure for connecting with the feeder used for the gastrointestinal tract is arranged at one end of the cap body 2 which is not connected to the top lid 1, and the connecting structure may employ a connecting structure. The cap body 2 includes a first casing 2-1 and a second casing 2-2, the first casing 2-1 is fixedly connected to the top lid 1, and the connecting structure 2-5 is located in the second casing 2-2. One side of the second casing 2-2 which is not provided with the connecting structure 2-5 extends into the first casing 2-1, and a top face of the second casing 2-2 is provided with multiple serrated protrusions 2-3 in a circumferential direction. The side of the second casing 2-2 which is not provided with the connecting structure 2-5 is fixedly connected to the first casing 2-1 through 2 to 4 ribs or contact points 2-4, the ribs may be made into an integral structure with the first casing 2-1 and the second casing 2-2 through ultrasonic heat thermal bonding, and the ribs may also be integrally formed with the first casing 2-1 and the second casing 2-2. An inner side face of the top lid 1 is provided with multiple grooves 1-1 matching with the serrated protrusions 2-3, and the serrated protrusions 2-3 are located inside the grooves 1-1.

The above connecting structure may employ a connecting structure, such as the screw structure specified by standard ISO 80369-3.

When the cap is used, in a process of screwing the cap onto a head portion of the feeder, since the grooves 1-1 of the top lid 1 of the cap and the serrated protrusions 2-3 on the top face of the second casing 2-2 are mutually engaged and locked, an acting force during the screwing process is applied mainly to the second casing 2-2 and the top lid 1, rather than the ribs (or the contact points) connecting the first casing 2-1 and the second casing 2-2. Therefore, the first casing 2-1 will and the second casing 2-2 will neither move with respect to each other nor be separated from each other due to the rotation, and thus the cap sealed on the head portion of the feeder remains intact during and after the screwing process. When the cap is unscrewed from the head portion of the feeder, since both the grooves 1-1 of the top lid 1 of the cap and the serrated protrusions 2-3 on the top face of the second casing are arranged in a forward-slanted tooth shape in a direction that the cap is unscrewed, the serrated protrusions 2-3 are separated from the grooves 1-1 during the process that the cap is unscrewed from the head portion of the feeder, and a sliding thrust is generated on slanted surfaces where the serrated protrusions and the grooves are in contact with each other. The sliding thrust and a rotating force act on the ribs (or the contact points) between the first casing and the second casing at the same time, causing the fragile ribs or contact points to be broken, and thus the first casing together with the top lid are separated from the second casing, and only the second casing is left for sealing the head portion of the feeder. In this case, a clinician authorized for feeding in the ward can easily identify whether the feeder has been tampered or not, and if the first casing 2-1 of the cap is broken or missing, the clinician will immediately find that the feeder has been tampered and will not use it, thus avoiding the risks of cross use or reuse, as well as the risks that pharmaceuticals may be transferred, replaced or abused, and thereby effectively ensuring the safety and reliability of the clinical use of sterile pharmaceutical preparations and feeders. In addition, when the authorized clinician in the ward gets the feeder with the intact sealing cap, under the controlled management of the authorized clinician, the cap having only the second casing 2-1 left after the cap is opened can still ensure the sealing of the head portion of the feeder. In this way, the self-destruct-upon-opening cap is not only beneficial for identifying whether the feeder is tampered, but also facilitates the authorized clinician to carry out clinical operations.

Second Embodiment

A difference between Embodiment 2 and Embodiment 1 is as follows. In Embodiment 2, serrated protrusions 2-3 are provided on the inner side face of the top lid in the circumferential direction, and grooves 1-1 matching with the serrated protrusions 2-3 are provided at the top face of the second casing. The principle of Embodiment 2 is the same as or similar to that of Embodiment 1, which will not be described herein.

The embodiments described hereinbefore are only the embodiments of the present application, and the description is specific and detailed, which cannot be understood as the limitation of the scope of the present application. It should be noted that, many modifications and improvements can be made by those skilled in the art without departing from the concept of the present application, and all these modifications and improvements belong to the protection scope of the present application.

What is claimed is:

1. A self-destruct-upon-opening cap applicable to a small-diameter connector used for a gastrointestinal tract, comprising:
    a top lid and a cap body, wherein the top lid is arranged on the cap body and is fixedly connected to the cap body,
    a connecting structure configured for matching and connecting with the small-diameter connector used for the gastrointestinal tract is arranged at one end of the cap body which is not connected to the top lid;
    wherein the cap body comprises a first casing and a second casing, and the first casing is fixedly connected to the top lid;
    wherein the connecting structure is located in the second casing; and
    wherein one side of the second casing which is not provided with the connecting structure extends into the first casing and is fixedly connected to the first casing through ribs or contact points;
        wherein a top face of the second casing is provided with serrated protrusions in a circumferential direction, an inner side face of the top lid is provided with grooves matching with the serrated protrusions, and the serrated protrusions are located inside the grooves; or
        the top face of the second casing is provided with the grooves in the circumferential direction, the inner side face of the top lid is provided with the serrated protrusions matching with the grooves, and the serrated protrusions are located inside the grooves.

2. The self-destruct-upon-opening cap according to claim 1, wherein the connecting structure is a threaded structure.

3. The self-destruct-upon-opening cap according to claim 2, wherein the threaded structure is connected to the small-diameter connector used for the gastrointestinal tract.

4. The self-destruct-upon-opening cap according to claim 3, wherein each of the grooves is a concave slope structure, the grooves are arranged in a forward-slanted tooth shape in one direction of the circumferential direction, and in a backward-slanted tooth shape in another reversed direction of the circumferential direction.

5. The self-destruct-upon-opening cap according to claim 2, wherein each of the grooves is a concave slope structure, the grooves are arranged in a forward-slanted tooth shape in one direction of the circumferential direction, and in a backward-slanted tooth shape in another reversed direction of the circumferential direction.

6. The self-destruct-upon-opening cap according to claim 1, wherein each of the grooves is a concave slope structure, the grooves are arranged in a forward-slanted tooth shape in one direction of the circumferential direction, and in a backward-slanted tooth shape in another reversed direction of the circumferential direction.

* * * * *